United States Patent
Justus et al.

(10) Patent No.: US 12,208,218 B2
(45) Date of Patent: Jan. 28, 2025

(54) TAMPER-EVIDENT ENCLOSURE FOR PICC LINE

(71) Applicants: Michael Justus, Beloit, WI (US); Jesse Justus, Sheboygan, WI (US); Katherine Justus, Sheboygan, WI (US)

(72) Inventors: Michael Justus, Beloit, WI (US); Jesse Justus, Sheboygan, WI (US); Katherine Justus, Sheboygan, WI (US)

(*) Notice: Subject to any disclaimer, the term of this patent is extended or adjusted under 35 U.S.C. 154(b) by 140 days.

(21) Appl. No.: 18/187,565

(22) Filed: Mar. 21, 2023

(65) Prior Publication Data
US 2023/0218859 A1     Jul. 13, 2023

Related U.S. Application Data

(63) Continuation of application No. 16/774,680, filed on Jan. 28, 2020, now Pat. No. 11,607,522.

(60) Provisional application No. 62/862,614, filed on Jun. 17, 2019.

(51) Int. Cl.
*A61M 25/00* (2006.01)
*A61M 39/10* (2006.01)

(52) U.S. Cl.
CPC ...... *A61M 25/002* (2013.01); *A61M 39/1011* (2013.01); *A61M 2039/1066* (2013.01); *A61M 2207/00* (2013.01)

(58) Field of Classification Search
CPC .......... A61M 25/02; A61M 2025/0246; A61M 2025/028; A61M 2039/0288; A61M 2205/273; A61M 2205/276; A61M 2205/27

See application file for complete search history.

(56) References Cited

U.S. PATENT DOCUMENTS

| 3,556,387 | A | * | 1/1971 | Trimble | B65D 85/324 |
|---|---|---|---|---|---|
|  |  |  |  |  | 206/521.8 |
| 3,767,110 | A | * | 10/1973 | Congleton | B65D 43/162 |
|  |  |  |  |  | 220/4.23 |
| 4,397,647 | A | * | 8/1983 | Gordon | A61M 25/02 |
|  |  |  |  |  | 128/DIG. 26 |
| 4,517,971 | A | * | 5/1985 | Sorbonne | A61M 25/02 |
|  |  |  |  |  | 604/174 |
| 4,782,977 | A | * | 11/1988 | Watanabe | B65D 55/024 |
|  |  |  |  |  | 292/307 R |

(Continued)

*Primary Examiner* — Scott J Medway
(74) *Attorney, Agent, or Firm* — Ryuh Patent Law; Steven Yu

(57) ABSTRACT

A catheter enclosure device for locking an intravenous catheter therein with tamper-evident features to deter unauthorized use. The catheter enclosure device may be particularly useful for peripherally inserted central catheters (PICC). The enclosure device comprises an open-top box and a removable lid for covering the box. The open-top box has a compartment for holding the proximal end of an intravenous catheter. The lid comprises a panel for covering the open portion of the open-top box and a folding wing that overhangs the forward end of the box when covering the box. The folding wing further comprises a retaining anchor. When the folding wing is folded down, the retaining anchor inserts into a locking slot on the forward end of the box, thereby preventing the lid from being removed off the box. Also disclosed are methods for using the catheter enclosure device.

13 Claims, 9 Drawing Sheets

(56) References Cited

U.S. PATENT DOCUMENTS

| | | | | |
|---|---|---|---|---|
| 4,917,261 A * | 4/1990 | Borst | B65D 43/162 | |
| | | | D7/538 | |
| 4,986,438 A * | 1/1991 | Borst | B65D 45/20 | |
| | | | 229/406 | |
| 5,040,695 A * | 8/1991 | Adams | B65D 43/162 | |
| | | | 220/837 | |
| 5,112,313 A * | 5/1992 | Sallee | A61M 25/02 | |
| | | | D24/130 | |
| 5,118,148 A * | 6/1992 | De Lima Castro Netto | | |
| | | | G09F 3/20 | |
| | | | 292/307 R | |
| 5,133,470 A * | 7/1992 | Abrams | B29C 66/549 | |
| | | | 215/250 | |
| 5,667,094 A * | 9/1997 | Rapchak | B65D 43/162 | |
| | | | 220/834 | |
| 5,890,648 A * | 4/1999 | Cai | B65D 5/48018 | |
| | | | 229/148 | |
| 5,906,292 A * | 5/1999 | Rider, Jr. | B65D 43/162 | |
| | | | 206/508 | |
| 6,715,632 B2 * | 4/2004 | Baker | B65D 43/22 | |
| | | | 220/4.23 | |
| 6,814,225 B2 * | 11/2004 | Belden, Jr. | E05B 73/0023 | |
| | | | 220/326 | |
| 8,056,750 B2 * | 11/2011 | Vovan | B65D 43/0235 | |
| | | | 220/268 | |
| 8,181,847 B1 * | 5/2012 | Erdie | B65D 43/021 | |
| | | | 229/125.17 | |
| 8,556,859 B2 * | 10/2013 | Nilson | A61M 25/02 | |
| | | | 604/174 | |
| 8,771,231 B2 * | 7/2014 | Makino | A61M 25/02 | |
| | | | 604/177 | |
| 8,795,580 B2 * | 8/2014 | Sellari | B65D 55/024 | |
| | | | 264/553 | |
| 9,944,436 B2 * | 4/2018 | Kalmanides | B65D 43/0268 | |
| 10,752,407 B1 * | 8/2020 | Nelson | B65D 85/345 | |
| 11,351,352 B1 * | 6/2022 | Kreatsoulas | A61M 25/02 | |
| 2005/0017007 A1 * | 1/2005 | Sellari | B65D 43/021 | |
| | | | 220/270 | |
| 2007/0043326 A1 * | 2/2007 | Navarro | A61M 25/02 | |
| | | | 604/264 | |
| 2009/0206082 A1 * | 8/2009 | Vovan | B65D 43/0249 | |
| | | | 29/428 | |
| 2011/0208132 A1 * | 8/2011 | Clark | A61M 39/1011 | |
| | | | 604/257 | |
| 2012/0103990 A1 * | 5/2012 | McCumber | B65D 41/165 | |
| | | | 220/270 | |
| 2014/0303595 A1 * | 10/2014 | Justus | A61M 5/5086 | |
| | | | 604/111 | |
| 2015/0060455 A1 * | 3/2015 | Chou | B65D 77/2016 | |
| | | | 220/270 | |
| 2017/0165437 A1 * | 6/2017 | Lopansri | A61M 5/002 | |
| 2019/0388652 A1 * | 12/2019 | Albany | A61M 25/02 | |
| 2020/0115117 A1 * | 4/2020 | Tsertsvadze | B65D 43/0235 | |

* cited by examiner

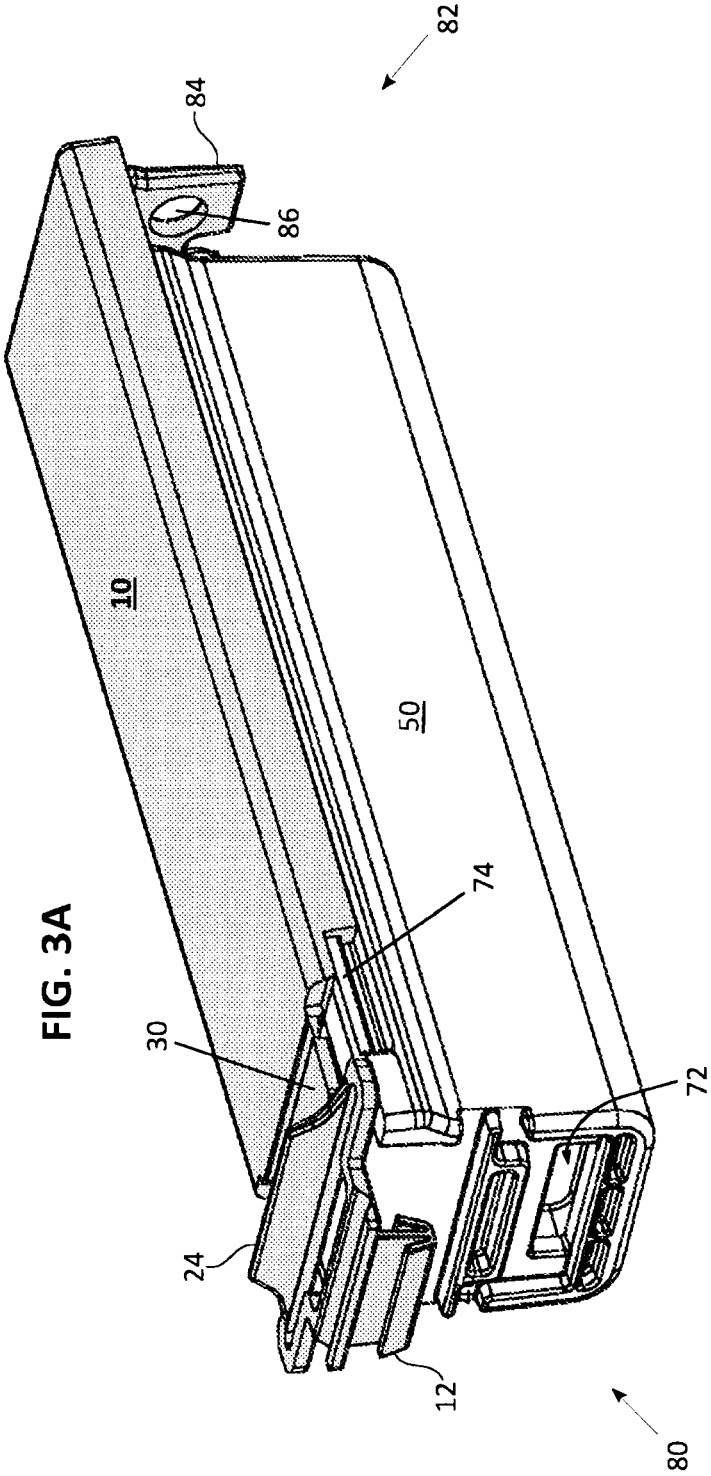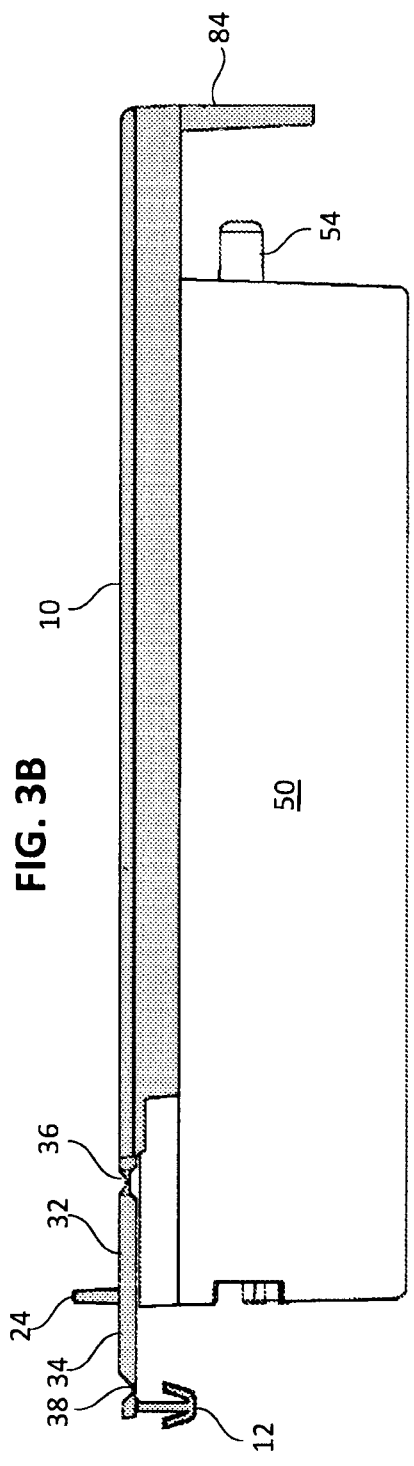

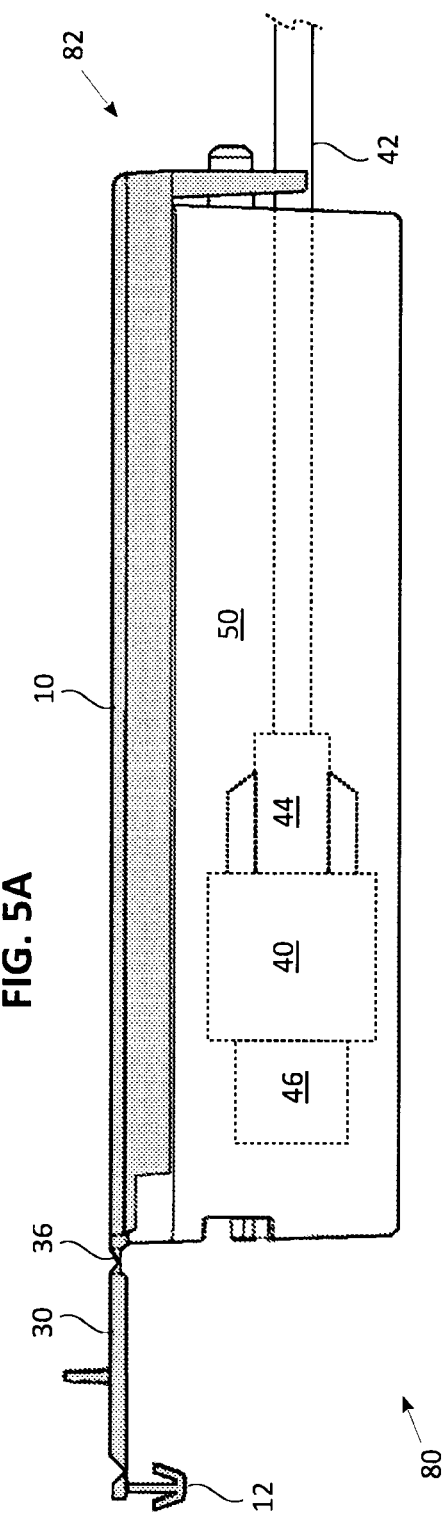
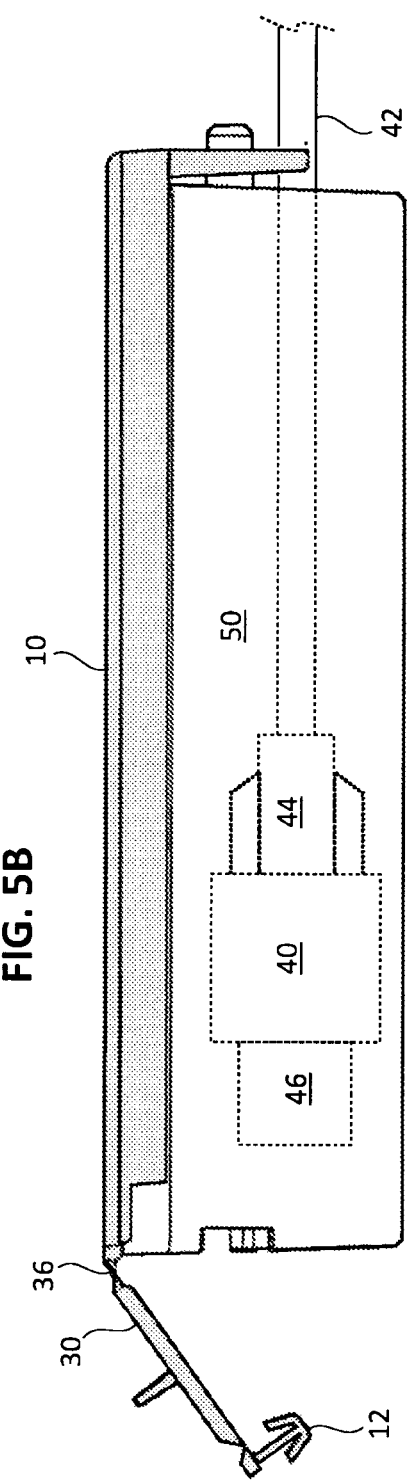

TAMPER-EVIDENT ENCLOSURE FOR PICC LINE

TECHNICAL FIELD

This invention relates generally to intravenous catheters, and more particularly to accessory devices to prevent unauthorized use thereof for self-administering illicit drugs.

BACKGROUND

After receiving intravenous (IV) medications in the hospital setting and upon discharge from the hospital, many patients will continue to need IV infusion of the medication for a prolonged time in the outpatient or home setting after discharge from the hospital. Examples of such situations include extended antibiotic therapy or long chemotherapy regimens. For providing easy IV access for long-term use, an indwelling IV catheter may be implanted into the patient. Examples of such types of catheters include central venous access catheters, peripherally inserted central catheters (PICC), and midline catheters.

However, providing convenient IV access can be a serious hazard for patients who are habitual drug abusers. Away from clinical supervision, the patient may covertly use this catheter to self-administer illicit drugs, such as opioid narcotics. In such situations, the patient may need to stay under clinical supervision, such as remaining hospitalized or being kept at a nursing facility, that is otherwise medically unnecessary. This represents a less than optimal utilization of healthcare resources. Thus, there is a need for making IV catheters, such as PICC lines, more resistant to unauthorized use.

SUMMARY

The present invention provides a catheter enclosure device for an intravenous catheter. In one aspect, the present invention is a catheter enclosure device that comprises an open-top box and a removable lid for covering the box. The open-top box has a compartment for holding the proximal end of an intravenous catheter, including the catheter port and the catheter hub. The enclosure device may be designed for any of various types of intravenous catheters, including standard peripheral venous catheters, central venous access catheters, peripherally inserted central catheters (PICC), and midline catheters.

The open-top box (and the enclosure device as a whole) has a forward end and a tail end. The tail end is the direction in which the intravenous line of the catheter exits the enclosure device. The forward end is the opposite direction, that is, the direction towards where the catheter port resides. The shape and dimensions of the open-top box are designed to be suitable for holding the proximal end of the intravenous catheter, including the catheter port and the catheter hub. For example, the open-top box (and the enclosure device as a whole) could have a rectangular, oblong, or pod shape. In general, the longitudinal length of the open-top box is greater than the transverse width.

There are a range of dimensions suitable for design of the catheter enclosure device and its various components. The following are examples. The length of the open-top box could be in the range of 6-10 cm. The depth of the open-top box could be in the range of 1-3 cm. The transverse width of the open-top box could be in the range of 1-4 cm.

The catheter enclosure device further comprises a removable lid that is designed to cover the open-top box. The lid may engage with the open-top box by any suitable mechanism, including sliding mechanisms, snapping mechanisms, etc. The lid comprises a panel for covering the open portion of the open-top box and a folding wing that overhangs the forward end of the box when covering the box. The folding wing comprises a hinge that allows the folding wing to fold down over the forward end of the box. In some embodiments, the folding wing has notches on the lateral sides (i.e. left and right) of the hinge.

The folding wing comprises a first portion (e.g. upper portion) and a second portion (e.g. lower portion) that are connected by one or more bridge segments. In some embodiments, the one or more bridge segments are the sole connection between the first portion and the second portion of the folding wing. In some embodiments, the one or more bridge segments consists of two bridge segments on the lateral sides (left and right) of the folding wing. In some embodiments, there is a void between the first portion, the second portion, and the two bridge segments.

The folding wing further comprises a retaining anchor. In some embodiments, the retaining anchor is located on the underside of the folding wing. The retaining anchor is designed to fit into a locking slot on the forward end of the box when the folding wing is folded down. This locks the folding wing onto the forward end of the box, thereby preventing the lid from being removed off the box.

In some embodiments, the retaining anchor has a transverse width in the range of 0.5-2 cm. In some embodiments, the retaining anchor has a transverse width in the range of 30%-70% of the width of the folding wing. In some embodiments, there is a second hinge on the folding wing located between the aforementioned first hinge and the base of the retaining anchor. In some embodiments, the folding wing has notches on the lateral sides of the second hinge. The enclosure device and components thereof could be made of any suitable material, including plastic materials. Examples of plastic materials that could be used include polyethylene-vinyl-acetate (PEVA), polyethylene, polypropylene, etc.

In another aspect, the present invention is a method of enclosing a catheter port inside a catheter enclosure device. The catheter port of an intravenous catheter (along with the catheter hub) is placed inside the open-top box. The open-top box is covered with the lid such that the folding wing is at the forward end of the box with the folding wing overhanging the forward end. The folding wing is folded downward to cause the retaining anchor to insert into the locking slot.

In another aspect, the present invention is a method of accessing a catheter port held inside a catheter enclosure device. The user cuts the one or more bridge segments to separate the first portion (e.g. upper portion) from the second portion (e.g. lower portion). This may be performed with any suitable cutting or tearing instrument, such as scissor, knife, scalpel blade, or pliers. With the separation of the first portion from the second portion, the first portion is lifted while the separated second portion remains locked. The lid is removed to expose the catheter port inside the open-top box. The catheter port may then be removed from the open-top box.

In some embodiments, the one or more bridge segments consists of two bridge segments on the lateral sides of the folding wing. The user cuts the bridge segments on the left and right sides. This separates the first portion from the second portion, allowing the folding wing to be lifted open.

BRIEF DESCRIPTION OF THE DRAWINGS

FIG. 1A shows a perspective view of the catheter enclosure device in conjunction with an intravenous (IV) catheter; FIG. 1B shows the opposite perspective view.

FIG. 2A shows an edge-on side view; FIG. 2B shows an top view.

FIGS. 3A and 3B show the lid slidably engaged with the box. FIG. 3A shows a perspective view; FIG. 3B shows a side view.

FIG. 4A shows a perspective view; FIG. 4B shows a side view.

FIGS. 5A-5D show the mechanism for locking the lid via the folding wing. FIGS. 5A-5C show side views in conjunction with the catheter held inside the box; FIG. 5D shows a close-up, inside view of the anchor and slot at the forward end of the enclosure device.

FIGS. 6A and 6B show the face of the enclosure device at the forward end; FIG. 6C shows a side view.

DETAILED DESCRIPTION

To assist in understanding the invention, reference is made to the accompanying drawings to show by way of illustration specific embodiments in which the invention may be practiced. The drawings herein are not necessarily made to scale or actual proportions. For example, lengths and widths of the components may be adjusted to accommodate the page size.

Figure 1A:
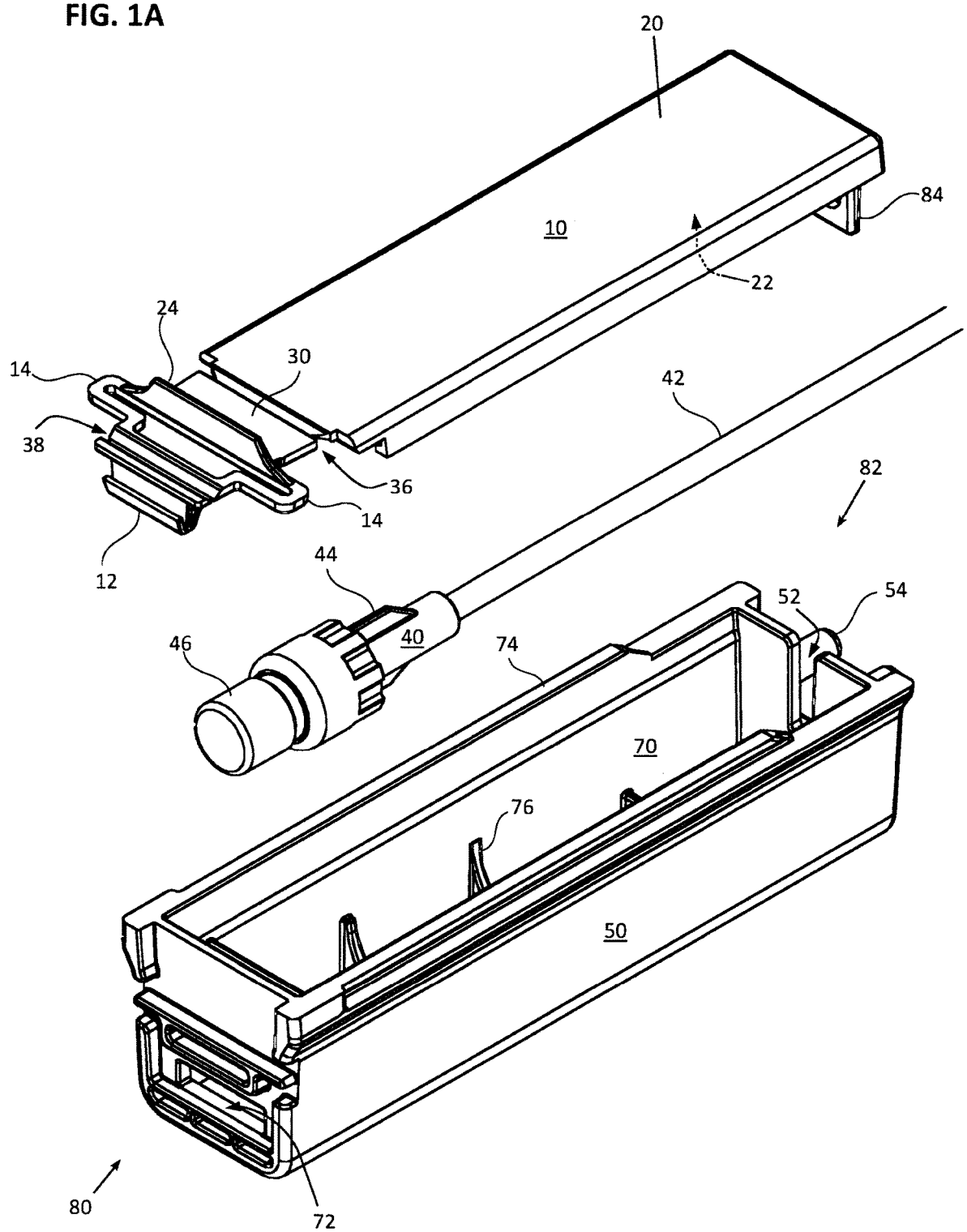
FIGS. 1A and 1B show an example of a catheter enclosure device of the present invention.
Figure 1B:
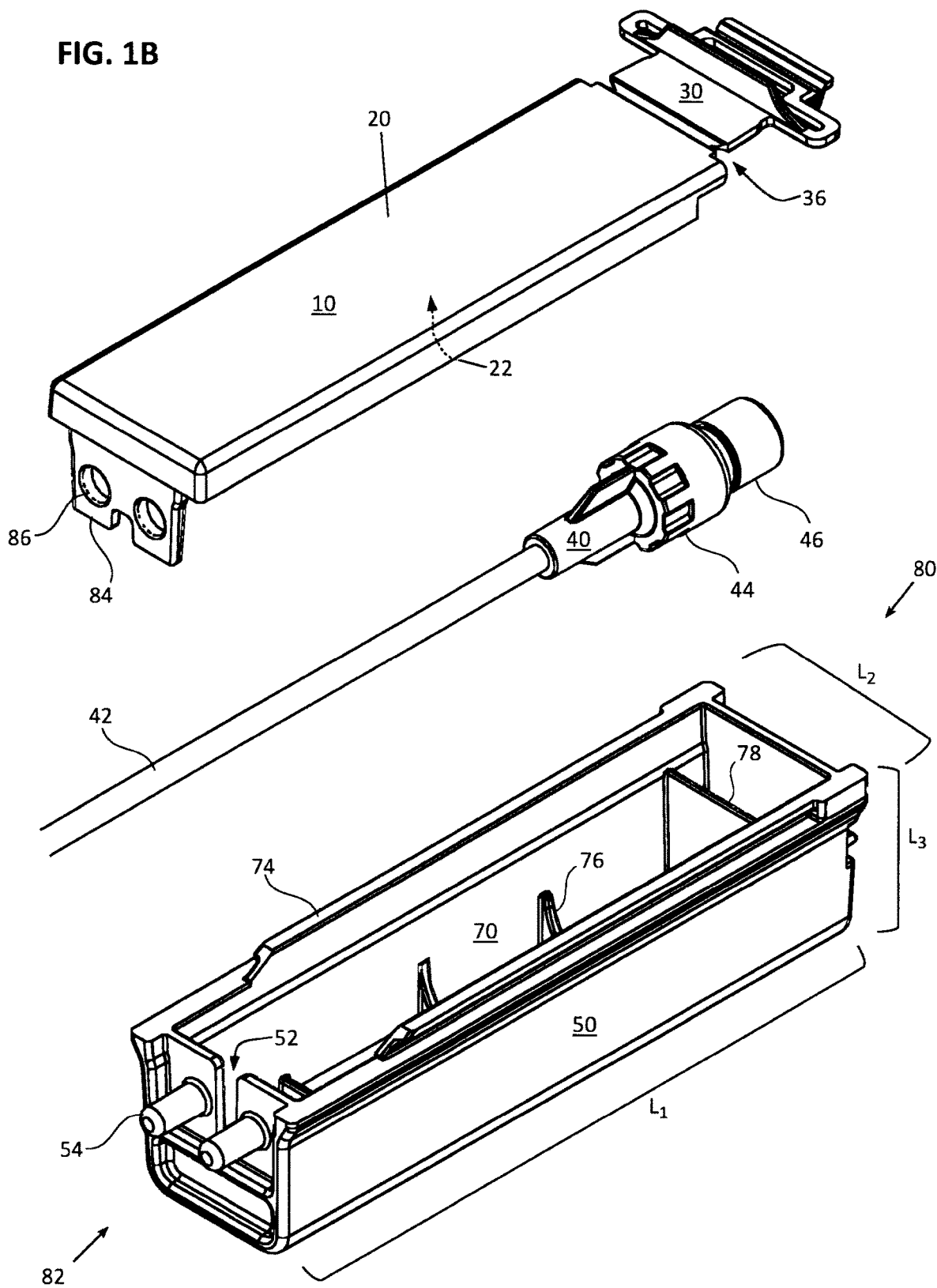

FIGS. 1A and 1B show an example of a catheter enclosure device of the present invention. FIG. 1A shows a perspective view of the catheter enclosure device in conjunction with an intravenous (IV) catheter 40; FIG. 1B shows the opposite perspective view. The IV catheter is not part of the enclosure device, but is shown here in conjunction with the enclosure device to help explain its function and features. The enclosure device comprises a coffin-like box 50 with an open top and a lid 10 that fits over the open-top box 50.

The open-top box 50 comprises a compartment 70 where the proximal end of the IV catheter 40 will reside. The catheter 40 comprises a port 46 (shown here with the protective cap on), a catheter hub 44, and an IV line 42. For designating orientation, the enclosure device has a forward end 80 and a tail end 82. The forward end 80 is towards where the catheter port 46 resides. The tail end 82 is towards where the IV line 42 of the catheter 40 exits from the enclosure device.

The dimensions of the open-top box 50 should be sufficiently large to accommodate the catheter hub 44 and the catheter port 46. Possible numeric ranges for the dimensions of the open-top box 50 are given in the "Summary" section above. In this specific example, the open-top box 50 has a length of about 79 mm (designated as $L_1$), width of about 21 mm (designated as $L_2$), and depth of about 17 mm (designated as $L_3$).

On the floor of the compartment 70 of the open-top box 50, there are ribs 76 that support the catheter port 46 and catheter hub 44. When the catheter 40 is residing inside the compartment 70, its catheter port 46 will abut against bulkhead 78 (best seen in FIG. 1B). The lid 10 is designed to fit onto the top of the box 50. There is a railing 74 for sliding engagement with the lid 10. On the forward end 80 face of the open-top box 50, there is a slot 72 for locking engagement with the wide-base anchor 12 of the lid 10. On the tail end 82 face of the open-top box 50, there is a narrow groove 52 through which the IV line 42 passes and exits the box 50. Groove 52 has a tapered V-shape to pinch close the IV line 42. The tail end 82 face also has a pair of alignment prongs 54 for securing the lid 10 shut.

The lid 10 serves as a cover for the open-top box 50. The lid 10 has an upper side 20 and underside 22. At its forward end 80, the lid 10 further comprises a folding wing 30 that is designed to fold by bending at a hinge 36. The hinge 36 on the folding wing 30 is a groove line of reduced thickness (i.e. conventionally referred to as a "living hinge"). As such, the folding wing 30 operates in a manner similar to a drop-leaf table. The wide-base anchor 12 is located on the underside 22 of the folding wing 30, whereas the grasping fin 24 is located on the upper side 20. When the folding wing 30 is fully folded down, the anchor 12 will lock into slot 72 on the forward end 80 face of the open-top box 50.

Figure 2A:
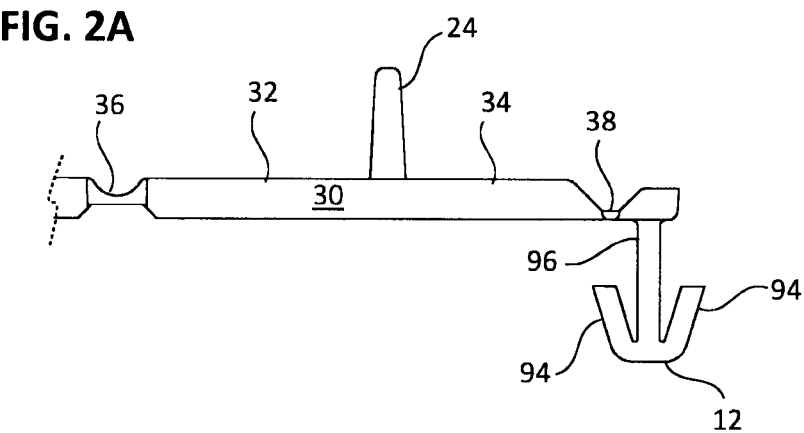
FIGS. 2A and 2B show close-up views of the folding wing.
Figure 2B:
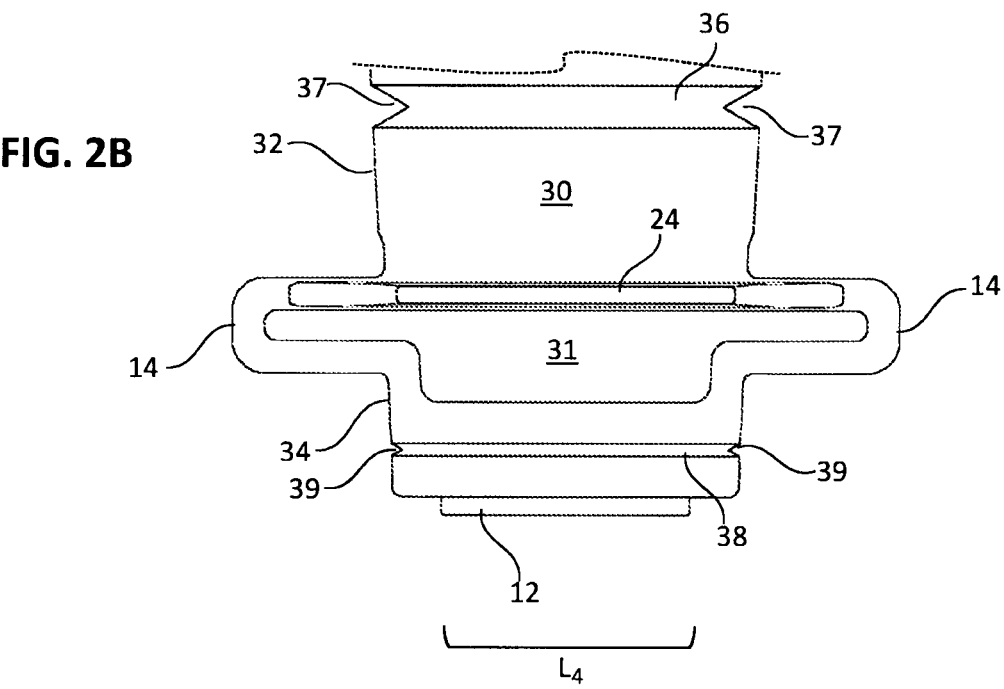

FIGS. 2A and 2B show close-up views of the folding wing 30. FIG. 2A shows an edge-on side view; FIG. 2B shows an top view. There are two hinges on folding wing 30; a primary hinge 36 and a secondary hinge 38. Both hinges are designed as "living hinges" where the panel has reduced thickness. Flexion of the folding wing 30 occurs primarily at hinge 36. Additionally, hinge 32 may also serve as a fault line where tearing, breakage, warping, or other deformation would occur during an unauthorized attempt to forcibly open the folding wing 30 when in its locked configuration. There are notches 37 on the lateral sides of hinge 36 to further promote its structural weakness as a fault line. Secondary hinge 38 located closer to the anchor 12 could serve as another line of flexion for the folded wing 30 and/or a fault line similar to hinge 36 as an indicator of attempt at tampering. There are also notches 39 on the lateral sides of hinge 38 to further promote its structural weakness as a fault line.

The sheet thickness at the hinges 36 and 38 could be selected on the basis of the desired amount of flexibility, resistance to tearing, durability, etc. Possible numeric ranges for the hinge thickness are given in the "Summary" section above. In this specific example, both hinges 36 and 38 are about 0.25 mm in sheet thickness. The folding wing 30 further comprises a fin 24 that is useful as a grasping point by the user.

The wide-base anchor 12 comprises a stem 96 and two flexible arms 94. As seen in the top view of FIG. 2B, the anchor 12 has a relatively wide base. Possible numeric ranges for the length of the base are given in the "Summary" section above. In this specific example, the anchor 12 has a base length (designated by $L_4$) of about 10 mm. This relatively wide base for anchor 12 helps to thwart any attempt to unlock the lid 10 by twisting the anchor 12 to snap it off its base on the underside of folding wing 30.

As seen in these figures, folding wing 30 can be considered as having two halves. There is an upper half 32 and a lower half 34. These two halves are connected by bridge segments 14 on each lateral side of the folding wing 30. The bridge segments 14 follow a path that creates a void window 31 in the folding wing 30. The sheet thickness at bridge segments 14 may be selected to facilitate cutting with scissor or knife. Possible numeric ranges for the bridge segment thickness are given in the "Summary" section above. In this specific example, both bridge segments 14 are about 0.9 mm thickness in sheet thickness. The function of the two halves 32 and 34, and the bridge segments 14 are be explained in more detail below.

FIGS. 3A and 3B show the lid 10 slidably engaged with the box 50. FIG. 3A shows a perspective view; FIG. 3B shows a side view. To avoid over-cluttering of the drawing, the catheter is not shown in these figures; but it is to be understood that the catheter is enclosed within the box 50 under lid 10. Starting from the tail end 82 of the open-top box 50, the lid 10 is made to engage the railing 74 on box 50. Once engaged with railing 74, the lid 10 is made to slide forward towards forward end 80.

Figure 4A:
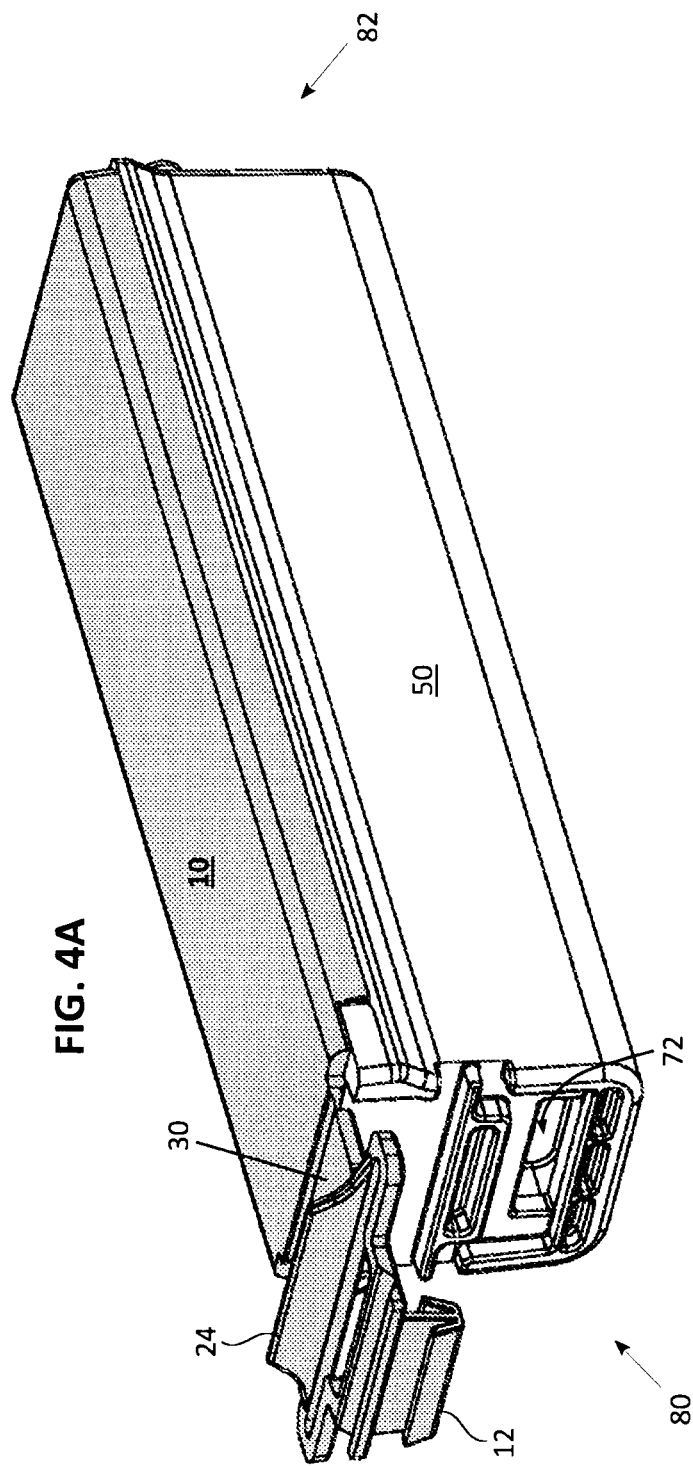
FIGS. 4A and 4B show the lid fully advanced to its closed position over open-top box.
Figure 4B:
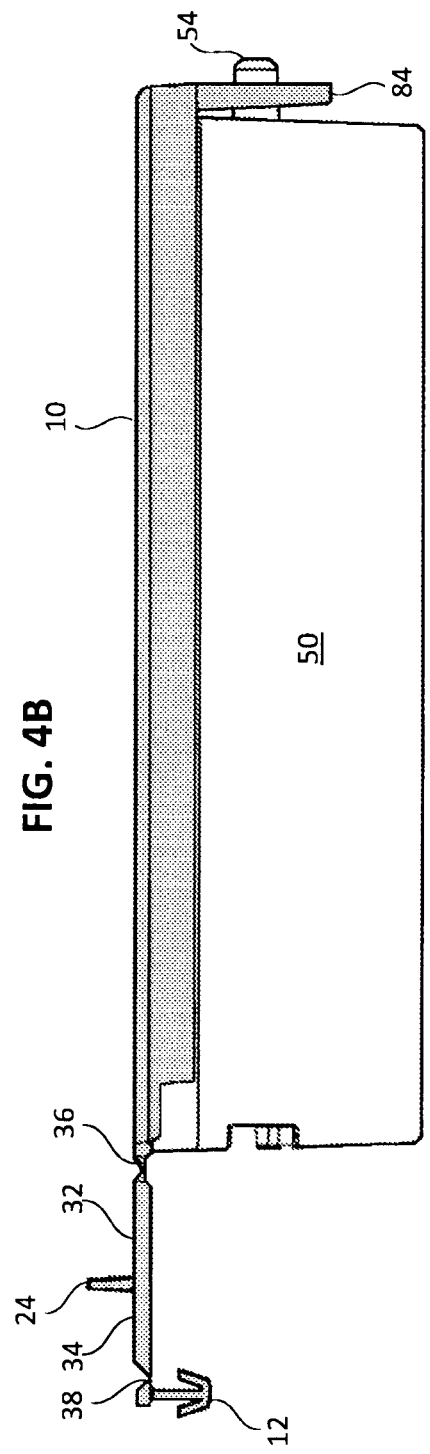

FIGS. 4A and 4B show the lid 10 fully advanced to its closed position over open-top box 50. FIG. 4A shows a perspective view; FIG. 4B shows a side view. The lid 10 is now in a position that allows folding wing 30 to be folded downward and locked into place.

Figure 5C:
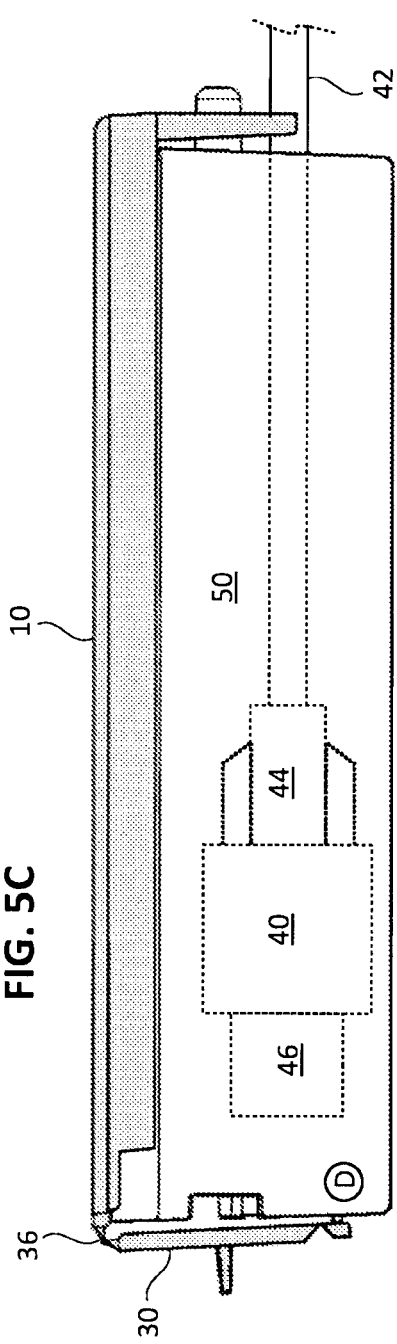
Figure 5D:
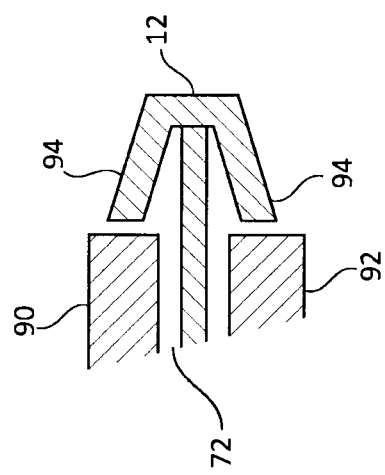

FIGS. 5A-5D show the mechanism for locking the lid 10 via the folding wing 30. FIGS. 5A-5C show side views in conjunction with the catheter 40 held inside the box 50; FIG. 5D shows a close-up, inside view of the anchor 12 and slot 72 at the forward end 80 of the enclosure device. As seen in FIG. 5A, the catheter 40 is enclosed within the enclosure device with the lid 10 fully covering the box 50. The port 46 of the catheter 40 is towards the forward end 80 and the IV line 42 exits out the tail end 82 of the enclosure device. In FIG. 5B, the folding wing 30 is made to bend downward with flexing at hinge 36. In FIG. 5C, the folding wing 30 is fully folded with the anchor 12 locked into the slot 72 at the forward end 80 face of the box 50.

FIG. 5D shows a close-up view of the anchor 12 locking mechanism that occurs inside box 50 at the location marked "D" in FIG. 5C. The flexible arms 94 of the anchor 12 bend inward as it slides through the slot 72. Upon being fully advanced into the slot 72, the arms 94 snap outward such that they are now retained by upper wall 90 and lower wall 92 of the slot 72. This makes the locking mechanism irreversible, such that the flexible arms 94 must be deformed or broken to open the folding wing 30, and thereby leaving evidence of tampering.

Figure 6A:
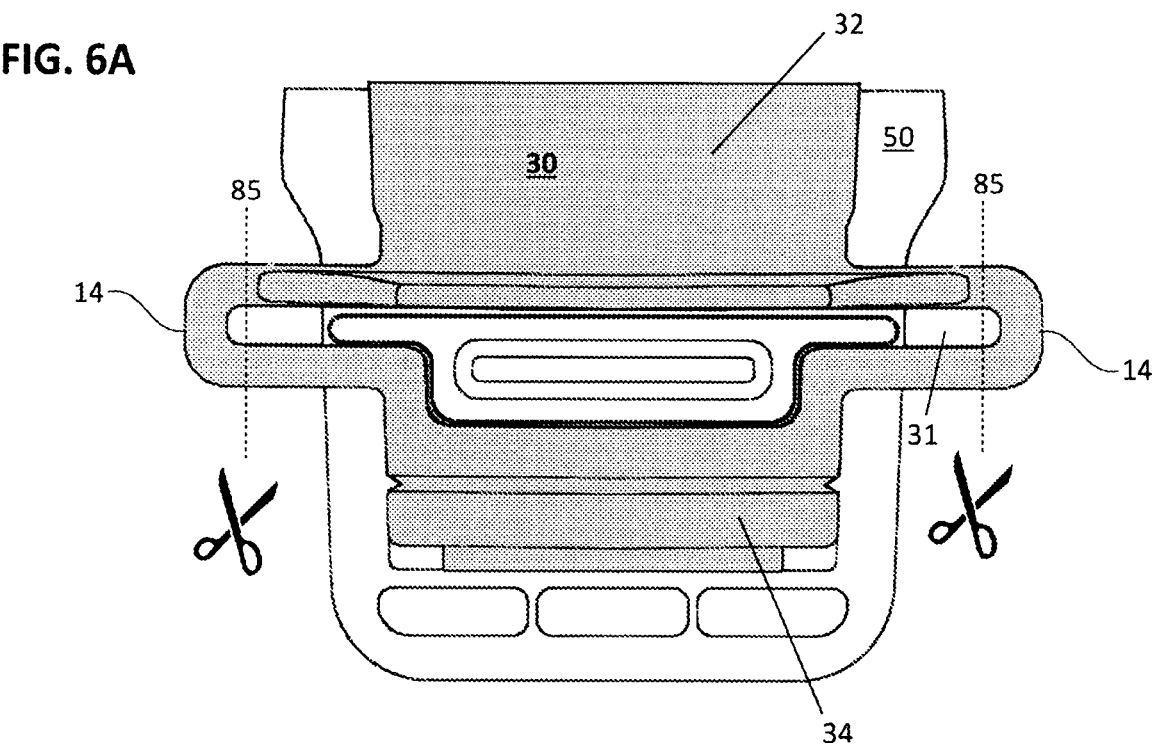
FIGS. 6A-6C show how an authorized user would open the locked enclosure device in the proper manner.
Figure 6B:
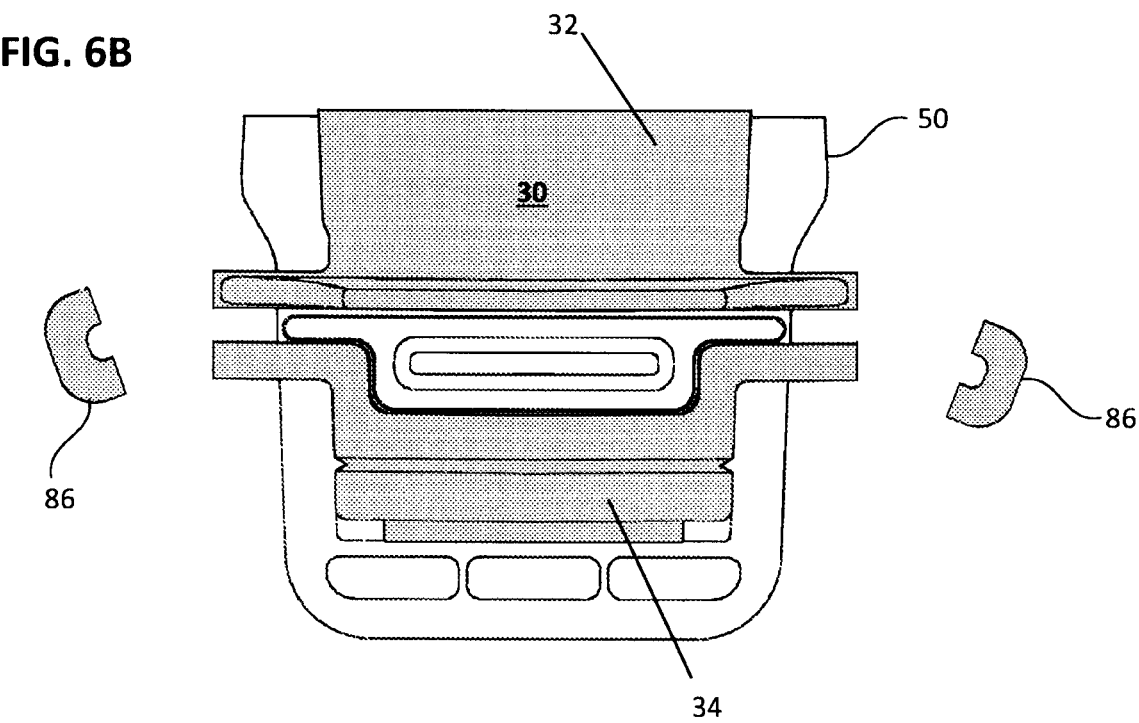
Figure 6C:
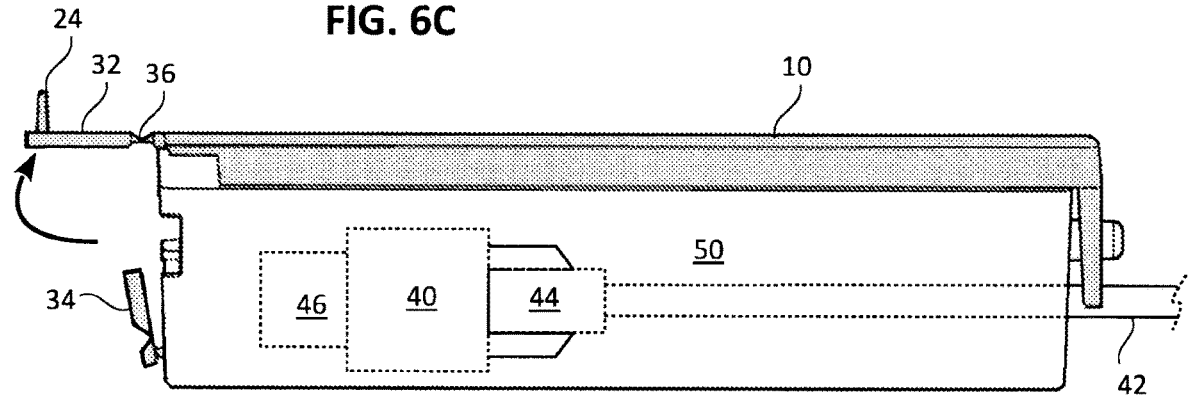

FIGS. 6A-6C show how an authorized user would open the locked enclosure device in the proper manner. FIGS. 6A and 6B show the face of the enclosure device at the forward end 80; FIG. 6C shows a side view. In FIG. 6A, the folding wing 30 has been folded down and locked into place. To open the enclosure device and access the catheter port, the authorized user cuts both bridging segments 14 with a scissor or knife shown as dotted line 85. As shown in FIG. 6B, this cutting results in fragments 86 with bridging segments 14 no longer connecting the upper half 32 and the lower half 34 of the folding wing 30 together. The void window 31 is now a complete separation between the upper half 32 and the lower half 34 of the folding wing 30. As shown in FIG. 6C, this releases the upper half 32 from its lock. The authorized user can grab the fin 24 on the upper half 32 to swing it upward and pull the lid 10 back towards the tail end 82 to open the enclosure device and expose the catheter port for authorized use.

The invention claimed is:

1. A method of enclosing a catheter port inside a catheter enclosure device, comprising:
    providing an intravenous catheter comprising the catheter port at a proximal end thereof and an intravenous line;
    providing a catheter enclosure device comprising:
    (i) a rectangular shaped open-top box having a compartment, a forward end having a locking slot, a tail end, a longitudinal length along an axis from the forward end to the tail end, and a transverse width; wherein the longitudinal length is greater than the transverse width;
    (ii) a removable lid for covering the box, wherein the lid is a separate component from the box and comprises a folding wing that overhangs the forward end of the box when covering the box, wherein folding wing comprises:
        (a) a hinge that allows the folding wing to fold down over the forward end of the box;
        (b) an upper portion and a lower portion;
        (c) one or more bridge segments connecting the upper portion to the lower portion;
        (d) a retaining anchor that fits into the locking slot when the folding wing is folded down;
    placing the catheter port of the intravenous catheter inside the compartment of the open-top box such that the catheter port points towards the forward end and the intravenous line towards the tail end;
    covering the open-top box with the lid such that the folding wing is at the forward end of the box and overhanging the forward end;
    (iii) folding the folding wing downward to cause the locking anchor to insert into the locking slot.

2. The method of claim 1, wherein the open-top box has a depth in the range of 1-3 cm, longitudinal length in the range of 6-10 cm, and transverse width in the range of 1-4 cm.

3. The method of claim 1, wherein the open-top box further comprises a groove opening at the tail end, and the method further comprises inserting the intravenous line into the groove opening.

4. The method of claim 3, wherein the groove opening has a tapered V-shape that pinches closed the intravenous line.

5. The method of claim 3, wherein covering the open-top box with the lid covers over the groove opening and traps the intravenous line within the groove opening.

6. The method of claim 1, further comprising accessing the catheter port by steps comprising:
    detaching the one or more bridge segments to separate the upper portion from the lower portion;
    lifting the upper portion of the folding wing;
    removing the lid to expose the catheter port.

7. The method of claim 6, wherein the lid is removed by sliding the lid towards the tail end.

8. The method of claim 6, further comprising removing the catheter port from the box.

9. The method of claim 6, wherein the folding wing of the lid further comprises a grasping fin on the upper portion of the folding wing.

10. The method of claim 9, wherein the step of lifting the upper portion of the folding wing comprises grasping the grasping fin and swinging the upper portion of the folding wing upward.

11. The method of claim 1, wherein the folding wing has notches on the lateral sides of the hinge.

12. The method of claim 1, wherein the one or more bridge segments of the folding wing are the sole connection between the upper portion and the lower portion of the folding wing.

13. The method of claim 1, wherein the hinge is a first hinge, and the folding wing further comprises a second hinge that is located between the first hinge and the base of the retaining anchor.

* * * * *